US00PP17608P2

(12) United States Plant Patent
Bergman

(10) Patent No.: US PP17,608 P2
(45) Date of Patent: Apr. 17, 2007

(54) ***HIBISCUS* PLANT NAMED 'YOHIB 2136'**

(50) Latin Name: *Hibiscus rosa-sinensis*
Varietal Denomination: YOHIB 2136

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 50 days.

(21) Appl. No.: 11/177,955

(22) Filed: Jul. 8, 2005

(51) Int. Cl.
*A01H 5/00* (2006.01)

(52) U.S. Cl. ..... Plt./257
(58) Field of Classification Search ..... Plt./257
See application file for complete search history.

(56) References Cited

PUBLICATIONS

UPOV–ROM Gtitm, Plant Variety Database, 2006/01, GTI Jouve Retrieval Software, Citation for *Hibiscus* 'Yohib 2136', 1 page.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct *Hibiscus* plant named 'YOHIB 2136', characterized by its compact, upright, outwardly spreading, uniform, dense and symmetrical plant habit that is appropriate for container production; glossy, palmately-lobed and dark green-colored leaves; uniform and freely flowering habit; white and pink bi-colored flowers with dark red-colored centers; good resistance to flower bud abscission during shipping; and tolerance to pathogens common to *Hibiscus* grown under Florida production conditions.

2 Drawing Sheets

Botanical designation: *Hibiscus rosa-sinensis.*
Cultivar denomination: 'YOHIB 2136'.

BACKGROUND OF THE INVENTION

The present invention relates to a new and distinct cultivar of *Hibiscus,* botanically known as *Hibiscus rosa-sinensis,* and hereinafter referred to by the name 'YOHIB 2136'.

The new *Hibiscus* is a product of a planned breeding program conducted by the Inventor in Alva, Fla. The objective of the breeding program is to create new freely-branching *Hibiscus* cultivars with a dense, uniform and compact plant habit appropriate for container production, early and uniform flowering, numerous flowers per lateral branch, desirable flower color and good postproduction longevity.

The new *Hibiscus* originated from a cross-pollination made by the Inventor in Alva, Fla. in early 1997, of a proprietary *Hibiscus rosa-sinensis* selection, designated as code number YB-1657, not patented, as the female, or seed, parent with a proprietary *Hibiscus rosa-sinensis* selection, designated as code number YB-1589, not patented, as the male, or pollen, parent. The cultivar YOHIB 2136 was discovered and selected by the Inventor as a flowering plant within the progeny of the stated cross-pollination in a controlled environment in Alva, Fla., on Oct. 21, 1998.

Asexual reproduction of the new *Hibiscus* by vegetative terminal cuttings in a controlled environment in Alva, Fla. since February, 1999, has shown that the unique features of this new *Hibiscus* are stable and reproduced true to type in successive generations.

SUMMARY OF THE INVENTION

The cultivar YOHIB 2136 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'YOHIB 2136'. These characteristics in combination distinguish 'YOHIB 2136' as a new and distinct cultivar:

1. Upright, outwardly spreading, uniform, dense and symmetrical plant habit that is appropriate for container production.
2. Glossy, palmately-lobed and dark green-colored leaves.
3. Uniform and freely flowering habit.
4. White and pink bi-colored flowers with dark red-colored centers.
5. Good resistance to flower bud abscission during shipping.
6. Tolerant to pathogens common to *Hibiscus* grown under Florida production conditions.

Plants of the new *Hibiscus* can be compared to plants of the female parent, the proprietary *Hibiscus* selection code number YB-1657. Plants of the new *Hibiscus* differ from plants of the female parent selection in the following characteristics:

1. Plants of the new *Hibiscus* are more vigorous than plants of the female parent selection.
2. Plants of the new *Hibiscus* and the female parent selection differ in flower coloration as plants of the female parent selection have a narrow white-colored margin.

Plants of the new *Hibiscus* can be compared to plants of the male parent, the proprietary *Hibiscus* selection code number YB-1589. Plants of the new *Hibiscus* differ from plants of the male parent selection in the following characteristics:

1. Plants of the new *Hibiscus* are more vigorous than plants of the male parent selection.
2. Plants of the new *Hibiscus* have palmately-lobed leaves whereas plants of the male parent selection have non-lobed leaves.
3. Flowers of plants of the new *Hibiscus* have imbricate petals whereas flowers of plants of the male parent selection do not have overlapping petals.
4. Plants of the new *Hibiscus* and the male parent selection differ in flower coloration as plants of the male parent selection have pink-colored flowers with burgundy-colored centers.

Plants of the new *Hibiscus* can be compared to plants of the *Hibiscus* cultivar Whirl Wind, disclosed in U.S. Plant Pat. No. 11,796. In side-by-side comparisons conducted in Alva, Fla., plants of the new *Hibiscus* differed from plants of the cultivar Whirl Wind in the following characteristics:

1. Plants of the new *Hibiscus* were more vigorous than plants of the cultivar Whirl Wind.
2. Flowers of plants of the new *Hibiscus* had imbricate petals whereas flowers of plants of the cultivar Whirl Wind did not have overlapping petals.
3. Plants of the new *Hibiscus* and the cultivar Whirl Wind differed in flower color as plants of the cultivar Whirl Wind had narrow white-colored margins.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus.*

The photograph on the first sheet comprises a side perspective view of five typical flowering plants of 'YOHIB 2136' grown in a container.

The photograph on the second sheet comprises a close-up view of a typical flower of 'YOHIB 2136'.

DETAILED BOTANICAL DESCRIPTION

The photographs and following observations, measurements and values describe plants grown in Alva, Fla., with five plants per 16.5-cm container in polyethylene-covered greenhouses during the late summer under conditions which closely approximate commercial production. During the production of the plants, day temperatures ranged from 16 to 37° C. and night temperatures ranged from 13 to 26° C. Plants were about four months old when the photographs and the description were taken. In the description, color references are made to The Royal Horticultural Society Colour Chart, 1995 Edition, except where general terms of ordinary dictionary significance are used.

Botanical classification: *Hibiscus rosa-sinensis* cultivar YOHIB 2136.

Parentage:

*Female or seed parent.*—Proprietary selection of *Hibiscus rosa-sinensis* designated as code number YB-1657, not patented.

*Male or pollen parent.*—Proprietary selection of *Hibiscus rosa-sinensis* designated as code number YB-1589, not patented.

Propagation:

*Type.*—By vegetative terminal cuttings.

*Time to initiate roots.*—About 10 days at temperatures of 24° C.

*Time to develop roots.*—About four weeks at temperatures of 24° C.

*Root description.*—Thick, fibrous; white in color.

*Rooting habit.*—Somewhat freely branching; moderately dense.

Plant description:

*Plant form and growth habit.*—Perennial, evergreen, upright, outwardly spreading, uniform, dense and symmetrical plant habit; inverted triangle. Vigorous growth habit.

*Branching habit.*—Freely branching, usually about three or four lateral branches develop after removal of terminal apex.

*Plant height.*—About 32 cm.

*Plant diameter* (*area of spread*).—About 39 cm.

*Lateral branch description.*—Length: About 28 cm. Diameter: About 5 mm. Internode length: About 3.2 cm. Strength: Strong, but flexible. Texture: Immature, pubescent; mature, woody and rough. Color: Immature: Close to 147A. Mature: Close to 195A to 197A.

*Foliage description.*—Arrangement: Alternate, single; numerous; symmetrical. Length: About 8.4 cm. Width: About 6.25 cm. Shape: Oak-leaf shape; palmately lobed. Apex: Acute; typically reflexed. Base: Cordate. Margin: Palmately lobed; serrate. Texture, upper and lower surfaces: Smooth to sparsely pubescent; rough; leathery. Luster, upper surface: Glossy. Luster, lower surface: Somewhat glossy. Venation pattern: Palmate. Color: Developing and fully expanded foliage, upper surface: More green than 147A. Developing and fully expanded foliage, lower surface: Close to 147A. Venation, upper surface: 147A to darker green than 147A. Venation, lower surface: Close to 147A to darker green than 146A. Petiole: Length: About 4.5 cm. Diameter: About 3 mm. Texture, upper and lower surfaces: Pubescent. Color, upper surface: 147A overlain with close to 187A. Color, lower surface: Close to 146A.

Flower description:

*Flower arrangement.*—Flowers arranged singly at terminal leaf axils. Freely flowering with usually about four flower buds and/or open flowers per terminal apex. Flowers face upright to outwardly.

*Flower appearance.*—Rounded, white and pink bi-colored flowers with dark red-colored centers. Flowers are open for about one to two days. Flowers persistent.

*Fragrance.*—None detected.

*Natural flowering season.*—Usually spring and summer or during periods of warm weather.

*Flower bud* (*before stage of showing color*).—Resistance to abscission during shipping: Plants of the new *Hibiscus* have been observed to resist flower bud drop when stored in a closed box for 5 days at 13° C. Length: About 3.1 cm. Diameter: About 1.3 cm. Shape: Ovoid. Color: Close to 146A.

*Flower diameter.*—About 12.75 cm.

*Flower length* (*height*).—About 8.7 cm.

*Petals.*—Arrangement: Corolla consists of five petals that are fused at base; petals imbricate. Length: About 8.25 cm. Width: About 5.5 cm. Shape:

Roughly obovate to spatulate. Apex: Rounded. Base: Attenuate. Margin: Entire; somewhat ruffled. Texture, upper and lower surfaces: Smooth, glabrous, satiny; center, waxy. Color: When opening and fully opened, upper surface: Towards the margins, close to 155D; towards the center, closer to 55A; center, close to 46A. When opening and fully opened, lower surface: Close to 155D.

*Sepals.*—Appearance: Five sepals fused into a tubular star-shaped calyx. Length: About 3.1 cm. Width: About 1 cm. Shape: Oblong. Apex: Cuspidate. Margin: Entire. Texture, upper surface: Smooth; waxy. Texture, lower surface: Sparsely pubescent. Color, upper surface: Close to 146B. Color, lower surface: Close to 146A.

*Flower bracts.*—Appearance: About six fused at base. Length: About 2.4 cm. Width: About 5 mm. Shape: Lanceolate. Apex: Sharply acute. Margin: Entire. Texture, upper surface: Smooth, glabrous. Texture, lower surface: Sparsely pubescent. Color, upper surface: Close to 146A. Color, lower surface: Darker green than 146A.

*Peduncles.*—Length: About 1.9 cm. Diameter: About 2.5 mm. Angle: Straight to slightly bent. Strength: Strong, flexible. Texture: Sparsely pubescent. Color: Close to 146A.

*Reproductive organs.*—Androecium: Stamen number: Numerous, about 50. Filament length: About 5 mm. Filament color: Close to 155D. Anther shape: Reniform. Anther size: About 2 mm by 1.5 mm. Anther color: Close to 155D. Amount of pollen: Abundant. Pollen color: Close to 15A. Gynoecium: Pistil length: About 8.7 cm. Style length: About 7.3 cm. Style texture: Smooth, waxy. Style color: Close to 155D; towards the base, close to 53A to 46A. Stigma appearance: Five, rounded. Stigma color: Close to 17A. Ovary color: Close to 154C.

*Seed/fruit.*—Seed and fruit production has not been observed.

Temperature tolerance: Plants of the new *Hibiscus* have been observed to tolerate temperatures from 0 to 38° C.

Disease/pest tolerance: Plants of the new *Hibiscus* grown under Florida production conditions have shown to be relatively tolerant to pathogens common to *Hibiscus* such as *Pseudomonas, Pythium* and *Phytophthora.* Plants of the new *Hibiscus* have not been observed to be tolerant to pests and other pathogens.

It is claimed:

1. A new and distinct *Hibiscus* plant named 'YOHIB 2136', as illustrated and described.

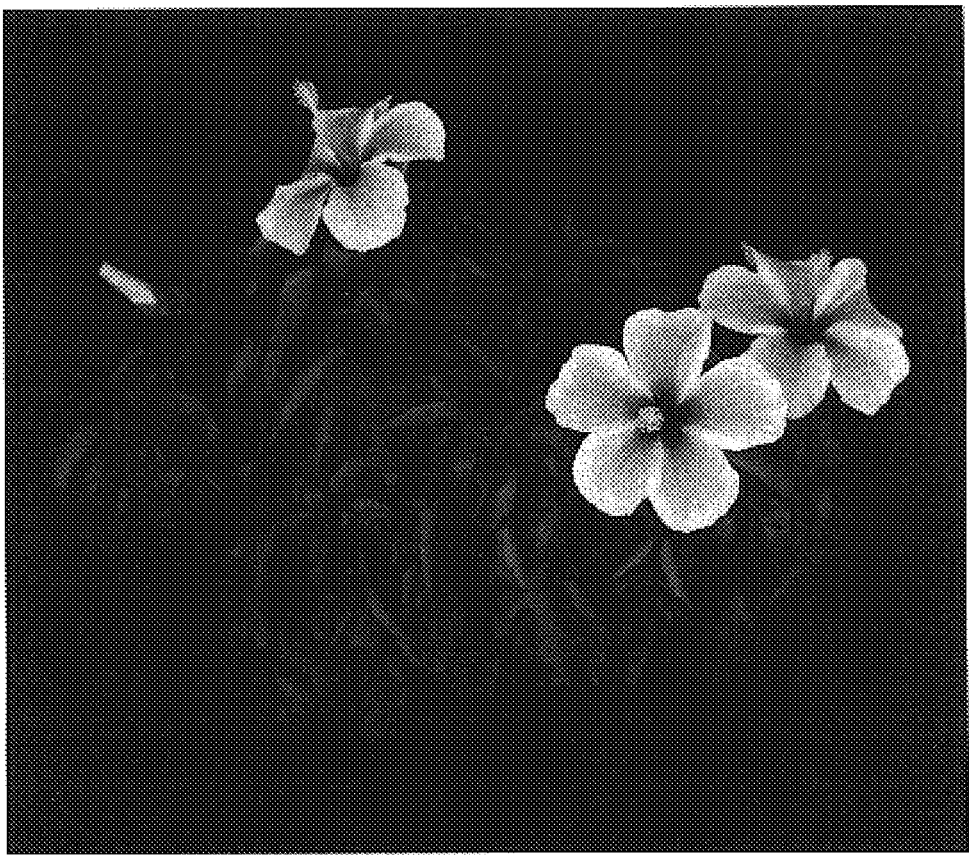

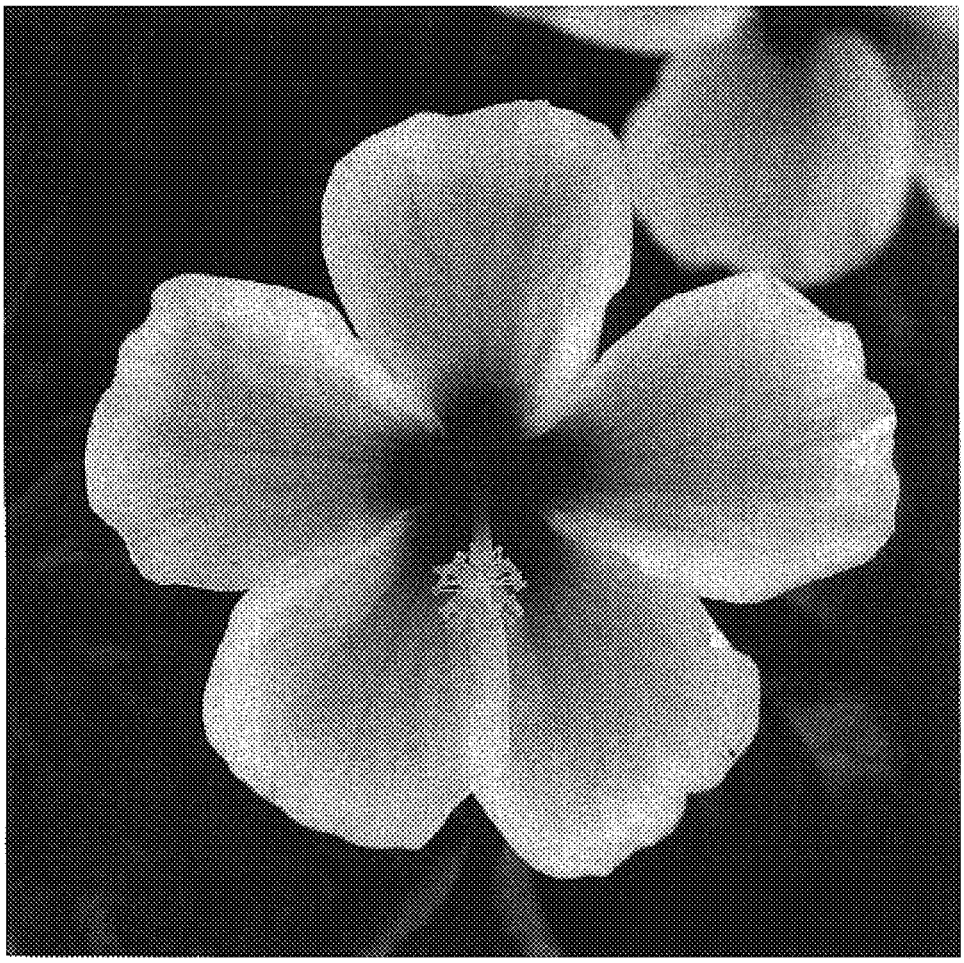

* * * * *